US00PP24526P2

(12) United States Plant Patent

Nishita et al.

(10) Patent No.: US PP24,526 P2
(45) Date of Patent: Jun. 3, 2014

(54) *PORTULACA* PLANT NAMED 'SAKPOR006'

(50) Latin Name: *Portulaca oleracea*
Varietal Denomination: SAKPOR006

(71) Applicant: Sakata Seed Corporation, Yokohama (JP)

(72) Inventors: Koichi Nishita, Kakegawa (JP); Michiyoshi Fuyama, Kakegawa (JP)

(73) Assignee: Sakata Seed Corporation, Yokohama (JP)

( * ) Notice: Subject to any disclaimer, the term of this patent is extended or adjusted under 35 U.S.C. 154(b) by 0 days.

(21) Appl. No.: 13/815,989

(22) Filed: Mar. 20, 2013

(51) Int. Cl.
*A01H 5/00* (2006.01)

(52) U.S. Cl.
USPC ..... Plt./471

(58) Field of Classification Search
USPC ..... Plt./471
See application file for complete search history.

(56) References Cited

U.S. PATENT DOCUMENTS

PP12,326 P2 * 1/2002 Matsukizono ..... Plt./471

OTHER PUBLICATIONS

Record Detail retrieved from UPOV Search on Sep. 10, 2013.*

* cited by examiner

*Primary Examiner* — Anne Grunberg
*Assistant Examiner* — Keith Robinson
(74) *Attorney, Agent, or Firm* — Barbara Campbell; Cochran Freund & Young LLC

(57) ABSTRACT

A *Portulaca* plant particularly distinguished by having a white flower color, flower blooming period from spring to fall and a semi-mounding, upright, and vigorous plant growth habit, is disclosed.

1 Drawing Sheet

Genus and species: *Portulaca oleracea.*
Variety denomination: 'SAKPOR006'.

BACKGROUND OF THE NEW PLANT

The present invention comprises a new and distinct variety of *Portulaca* plant, botanically known as *Portulaca oleracea*, and referred to by the variety name 'SAKPOR006'. 'SAKPOR006' originated from a hybridization in Kakegawa, Japan in 2006 between the female *Portulaca* line 'Mo04-19A-V2', an unpatented proprietary *Portulaca* breeding line having a white flower color and bushy growth habit, and the male *Portulaca* line 'BB03-36A-2-V4', an unpatented proprietary *Portulaca* breeding line with a rose flower color and bushy growth habit.

In August 2006, the female parent line 'Mo04-19A-V2' and male parent line 'BB03-36A-2-V4' were crossed and $F_1$ seeds were obtained. In May 2007, the $F_1$ seed was sown in the greenhouse, cultivated and plant lines were produced with rose, pink, and white flowers having a bushy plant habit. The plants were evaluated and plant line 'K2008-187' was selected for its white flower color, flower blooming period from spring to fall, and vigorous plant growth habit.

In May 2008, 'K2008-187' was vegetatively propagated, cultivated, and evaluated. In August 2008, 'K2008-187' was confirmed to be fixed and stable. In May 2009, May 2010, and May 2011, 'K2008-187' was vegetatively propagated to reconfirm its stability. 'K2008-187' was subsequently named 'SAKPOR006' and its unique characteristics were found to reproduce true to type in successive generations of asexual propagation via vegetative cuttings.

SUMMARY

The following are the most outstanding and distinguishing characteristics of this new variety when grown under normal horticultural practices in Salinas, Calif.

1. White flower color;
2. Flower blooming period from spring to fall; and
3. A semi-mounding, upright, and vigorous plant growth habit.

DESCRIPTION OF THE PHOTOGRAPHS

This *Portulaca* plant is illustrated by the accompanying photographs which show the plant's overall plant habit including form, foliage, and flowers. The photographs are of a twelve-month-old plant grown in Salinas, Calif. under greenhouse conditions in the fall of 2012. The colors shown are as true as can be reasonably obtained by conventional photographic procedures.

DESCRIPTION OF THE NEW VARIETY

Figure 1:
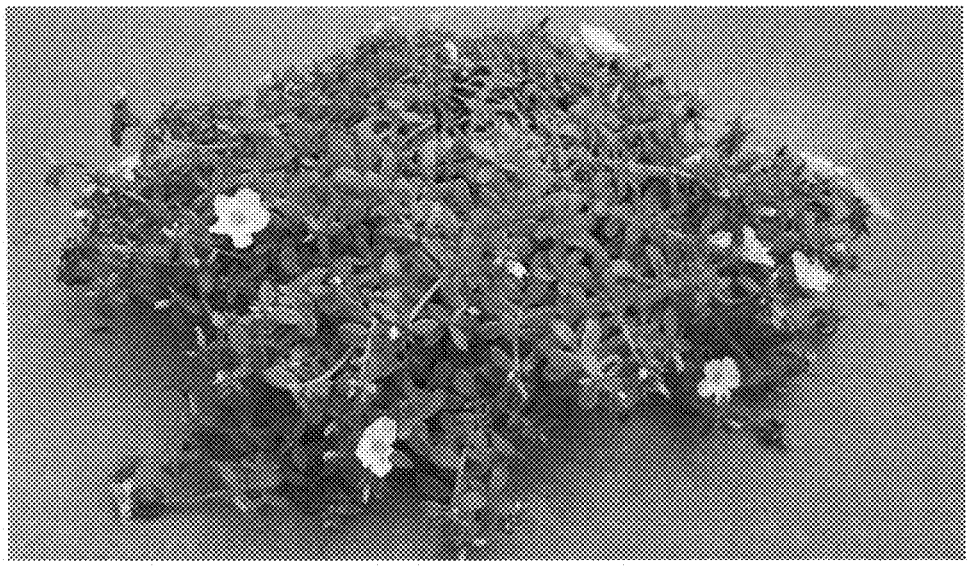
FIG. 1 shows the overall plant habit of the plant grown in a pot.
Figure 2:
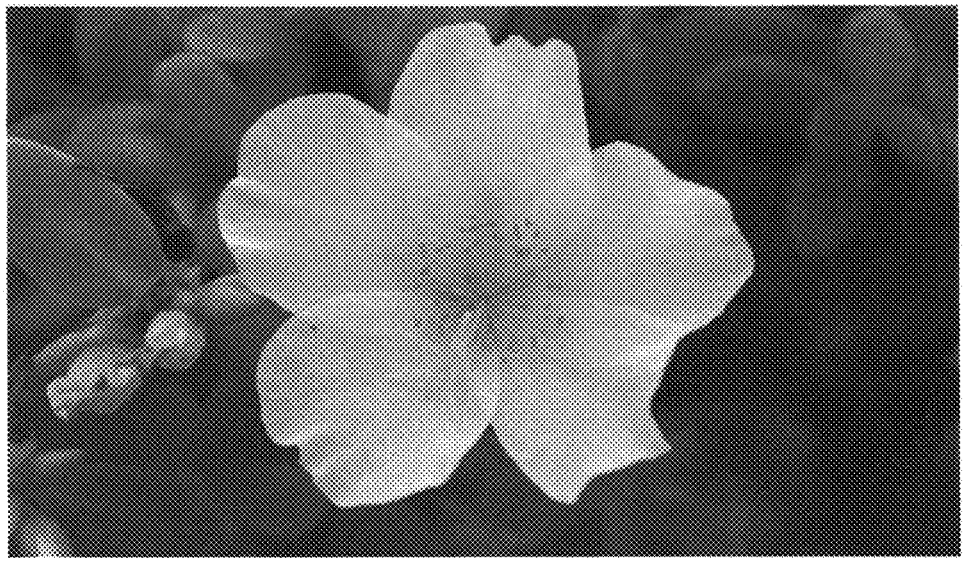
FIG. 2 shows a close-up of the mature inflorescence of the plant.

The following detailed descriptions set forth the distinctive characteristics of 'SAKPOR006'. The data which define these characteristics were collected from asexual reproductions carried out in Salinas, Calif. Data was collected on twelve-month-old plants grown under greenhouse conditions in Salinas, Calif. in the fall of 2012. Color references are to The R.H.S. Colour Chart of The Royal Horticultural Society of London (R.H.S.), $4^{th}$ edition (2001).

Classification:

*Family.*—Portulacaceae.
*Botanical.*—*Portulaca oleracea.*
*Common.*—Purslane.
*Designation.*—'SAKPOR006'.

Parentage:

*Female parent*.—Proprietary *Portulaca* line 'Mo04-19A-V2' (unpatented).

*Male parent*.—Proprietary *Portulaca* line 'BB03-36A-2-V4' (unpatented).

Growth:

*Time to produce a rooted cutting*.—About 2 weeks.

*Environmental conditions for plant growth*.—The terminal 1.0 to 1.5 inches of an actively growing stem was excised. The vegetative cuttings were propagated in five to six weeks. The base of the cuttings were dipped for 1 to 2 seconds in a 1:9 solution of Dip 'N Grow (1 solution: 9 water) root inducing solution immediately prior to sticking into the cell trays. Cuttings were stuck into plastic cell trays having 98 cells, and containing a moistened peat moss-based growing medium. The cuttings were misted with water from overhead for 10 seconds every 30 minutes until sufficient roots were formed. Rooted cuttings were transplanted and grown in 20 cm diameter plastic pots in a glass greenhouse located in Salinas, Calif. Pots contained a peat moss-based growing medium. Soluble fertilizer containing 20% nitrogen, 10% phosphorus and 20% potassium was applied once a day or every other day by overhead irrigation. Pots were top-dressed with a dry, slow release fertilizer containing 20% nitrogen, 10% phosphorus and 18% potassium. The typical average air temperature was 24° C.

Plant description:

*Habit and form*.—Semi-mounding, upright, and vigorous.

*Life cycle*.—Annual.

*Height* (*from soil line to top of foliage*).—Approximately 10.0 cm.

*Spread*.—Approximately 50.0 cm.

*Flowering requirements*.—Blooms repeatedly from spring to fall.

Stems:

*General description*.—Round, slightly rough with lateral ridges.

*Stem length*.—14.0 cm.

*Diameter*.—0.3 cm.

*Internode length* (*average*).—2.0 cm.

*Color*.—RHS 146C (Yellow-Green) with RHS 182B (Greyed-Red) anthocyanin.

*Pubescence*.—Absent.

*Anthocyanin color*.—RHS 182B (Greyed-Red).

*Branching*.—Abundant.

Leaves:

*Arrangement*.—Alternate.

*Shape*.—Oblanceolate with cuspidate tip in mature leaves and acute tips in younger leaves near the apex of the stem.

*Apex*.—Acute.

*Base*.—Rounded.

*Margin*.—Entire.

*Surface appearance* (*both surfaces*).—Dull.

*Surface texture* (*both surfaces*).—Smooth, no pubescence.

*Length*.—1.9 cm.

*Width*.—0.9 cm.

*Thickness*.—0.1 cm.

*Color*.—Upper surface: Closest to RHS 146C (Yellow-Green). Lower surface: Closest to RHS 146D (Yellow-Green).

*Venation*.—Absent.

*Petiole*.—Absent.

*Fragrance*.—Absent.

Inflorescence:

*Inflorescence type*.—Solitary, sessile.

*Flowering habit*.—Determinate.

*Time to bloom from propagation*.—6 to 8 weeks.

*Lastingness of individual blooms on the plant*.—1 day.

*Fragrance*.—Absent.

Flower bud:

*Surface appearance and texture*.—Shiny, pubescent.

*Length*.—0.7 cm.

*Diameter*.—0.4 cm.

*Shape*.—Lanceolate.

*Color*.—RHS 143B (Green).

Corolla:

*Shape*.—Five distinct petals, free with an indent at tip of petal.

*Flower diameter*.—3.2 cm.

*Flower depth*.—1.0 cm.

*Petals*.—Shape: Heart-shaped with a square base. Apex: Retuse. Base: Square. Margin: Double lobed, slightly sinuate. Surface texture (both surfaces): Glabrous. Length: 2.0 cm. Width: 1.3 cm. Color: Upper surface: RHS N155A (White) with RHS 145D (Yellow-Green) at the base. Lower surface: RHS N155A (White).

Calyx:

*Arrangement*.—Composed of two sepals, free.

*Sepals*.—Shape: Elliptic. Apex: Cuspidate. Margin: Entire, slightly sinuate. Color: Upper surface: RHS 146D (Yellow-Green). Lower surface: RHS 147D (Yellow-Green). Texture (both surfaces): Smooth. Appearance: Double lobed, slightly sinuate. Length: 0.9 cm. Diameter: 0.5 cm.

Reproductive organs: Androecium.

*Stamen number*.—Many.

*Stamen color*.—RHS 145D (Yellow-Green).

*Stamen form*.—Free.

*Stamen length*.—0.5 cm.

*Filament color*.—RHS 145D (Yellow-Green).

*Pollen color*.—RHS 17A (Yellow-Orange).

*Pollen amount*.—Abundant.

*Ovary diameter*.—0.3 cm.

*Ovary color*.—RHS 143B (Yellow-Green).

*Placental arrangement*.—Central.

*Pistil number*.—1 (per inflorescence).

*Pistil length*.—0.6 cm.

*Stigma color*.—RHS 145D (Yellow-Green).

*Stigma length*.—0.1 cm.

*Style length*.—0.2 cm.

*Style color*.—RHS 154D (Yellow-Green).

*Seed production*.—Absent.

Disease and insect resistance: None observed.

COMPARISON WITH PARENTAL LINES AND KNOWN VARIETY

'SAKPOR006' is a new and unique variety of *Portulaca* owing to its white flower color, flower blooming period from spring to fall and a semi-mounding, upright, and vigorous plant growth habit. 'SAKPOR006' is distinguished from its parents mainly by flower color and plant growth habit as shown in Table 1 below:

TABLE 1

| Comparison with Parental Lines | | | |
|---|---|---|---|
| Characteristic | 'SAKPOR006' | Female Parent 'Mo04-19A-V2' | Male Parent 'BB03-36A-2-V4' |
| Flower color | White | White | Rose |
| Plant growth habit | Semi-mounding, vigorous, upright | Bushy | Bushy |

'SAKPOR006' is a new and unique variety of *Portulaca* owing to its white flower color, flower blooming period from spring to fall and a semi-mounding, upright, and vigorous plant growth habit. 'SAKPOR006' is most similar to the commercial *Portulaca* variety 'DPAZ17', also commercially known as PAZZAZ™ 'Jumbo White', (U.S. Plant Pat. No. 23,245); however there are differences as described in Table 2 below.

TABLE 2

| Comparison with Similar Variety | | |
|---|---|---|
| Characteristic | 'SAKPOR006' | 'DPAZ17' |
| Flower petal color, upper surface | RHS N155A (White) with RHS 145D (Yellow-Green) at the base | Near RHS N155A (White) |
| Flower petal color, lower surface | RHS N155A (White) | Near RHS N155A (White) |
| Flower size (diameter) | 3.2 cm | 5.2 cm |
| Plant growth habit | Semi-mounding, upright, vigorous | Compact, semi-trailing |

We claim:

1. A new and distinct variety of *Portulaca* plant as shown and described herein.

* * * * *